(12) United States Patent
Gui et al.

(10) Patent No.: US 11,506,739 B2
(45) Date of Patent: Nov. 22, 2022

(54) SYSTEMS AND METHODS FOR GENERATING LOCALIZER SCAN SETTINGS FROM CALIBRATION IMAGES

(71) Applicant: GE Precision Healthcare LLC, Milwaukee, WI (US)

(72) Inventors: Dawei Gui, Sussex, WI (US); Dattesh Dayanand Shanbhag, Bangalore (IN); Chitresh Bhushan, Schenectady, NY (US); André de Almeida Maximo, Rio de Janeiro (BR)

(73) Assignee: GE Precision Healthcare LLC, Milwaukee, WI (US)

( * ) Notice: Subject to any disclaimer, the term of this patent is extended or adjusted under 35 U.S.C. 154(b) by 516 days.

(21) Appl. No.: 16/573,955

(22) Filed: Sep. 17, 2019

(65) Prior Publication Data
US 2021/0080531 A1 Mar. 18, 2021

(51) Int. Cl.
| | |
|---|---|
| *G01V 3/00* | (2006.01) |
| *G01R 33/58* | (2006.01) |
| *G01R 33/54* | (2006.01) |
| *A61B 5/055* | (2006.01) |
| *G06F 9/54* | (2006.01) |
| *G06N 3/08* | (2006.01) |
| *G06N 20/00* | (2019.01) |
| *A61B 5/00* | (2006.01) |

(52) U.S. Cl.
CPC ............ *G01R 33/58* (2013.01); *A61B 5/0033* (2013.01); *A61B 5/055* (2013.01); *G01R 33/543* (2013.01); *G06F 9/542* (2013.01); *G06N 3/084* (2013.01); *G06N 20/00* (2019.01)

(58) Field of Classification Search
CPC ............. G01R 33/3415; G01R 33/543; G01R 33/5659; G01R 33/36; A61B 5/055
USPC ........................................................ 324/307
See application file for complete search history.

(56) References Cited

U.S. PATENT DOCUMENTS

| | | | |
|---|---|---|---|
| 2005/0089135 A1* | 4/2005 | Toth ....................... | A61B 6/488 378/16 |
| 2006/0247513 A1* | 11/2006 | Wang ................... | G01N 23/046 600/410 |

(Continued)

OTHER PUBLICATIONS

Gui, D. et al., "Systems and Methods for Automated Graphical Prescription With Deep Neural Networks," U.S. Appl. No. 16/052,427, filed Aug. 1, 2018, 35 pages.

(Continued)

*Primary Examiner* — Walter L Lindsay, Jr.
*Assistant Examiner* — Frederick Wenderoth
(74) *Attorney, Agent, or Firm* — McCoy Russell LLP

(57) ABSTRACT

Methods and systems are provided for determining scan settings for a localizer scan based on a magnetic resonance (MR) calibration image. In one example, a method for magnetic resonance imaging (MRI) includes acquiring an MR calibration image of an imaging subject, mapping, by a trained deep neural network, the MR calibration image to a corresponding anatomical region of interest (ROI) attribute map for an anatomical ROI of the imaging subject, adjusting one or more localizer scan parameters based on the anatomical ROI attribute map, and acquiring one or more localizer images of the anatomical ROI according to the one or more localizer scan parameters.

20 Claims, 7 Drawing Sheets

(56) References Cited

U.S. PATENT DOCUMENTS

| | | | | |
|---|---|---|---|---|
| 2015/0054505 | A1* | 2/2015 | Wang | G01R 33/56545 |
| | | | | 324/309 |
| 2016/0358043 | A1* | 12/2016 | Mu | G06K 9/6217 |
| 2017/0281042 | A1* | 10/2017 | Miller | A61B 5/055 |
| 2017/0287174 | A1* | 10/2017 | Muslih | A61B 8/5246 |
| 2017/0364252 | A1* | 12/2017 | Deshpande | A61B 5/055 |

OTHER PUBLICATIONS

Maximo, A. et al., "Systems and Methods for Generating Diagnostic Scan Parameters From Calibration Images," U.S. Appl. No. 16/711,120, filed Dec. 11, 2019, 48 pages.

* cited by examiner

SYSTEMS AND METHODS FOR GENERATING LOCALIZER SCAN SETTINGS FROM CALIBRATION IMAGES

TECHNICAL FIELD

Embodiments of the subject matter disclosed herein relate to magnetic resonance imaging (MRI), and more particularly, to systems and methods for generating localizer scan settings from magnetic resonance (MR) calibration images using deep neural networks.

BACKGROUND

Medical imaging systems are often used to obtain internal physiological information of a subject, such as a patient. For example, a medical imaging system may be used to obtain images of the bone structure, the brain, the heart, the lungs, and various other features of a subject. Medical imaging systems may include magnetic resonance imaging (MRI) systems, computed tomography (CT) systems, x-ray systems, ultrasound systems, and various other imaging modalities.

Prior to performing a diagnostic scan of the subject, a fast, anatomy location blinded, thick slice scan or low-dose scan of the subject, often referred to as a scout scan or a localizer scan, may be performed to obtain localizer images of the subject's internal anatomy. The medical imaging system and/or operator of the medical imaging system may plan the diagnostic scan of the subject according to the localizer images, to ensure that the full-strength diagnostic scan of the subject correctly images the subject as desired. If the localizer images do not adequately show all aspects of the desired anatomy, the localizer scan may have to be re-performed to ensure the diagnostic scan is carried out correctly, which may prolong the diagnostic scan.

SUMMARY

In one embodiment, a method for magnetic resonance imaging (MRI) includes acquiring a magnetic resonance (MR) calibration image of an imaging subject, mapping, by a trained deep neural network, the MR calibration image to a corresponding anatomical region of interest (ROI) attribute map for an anatomical ROI of the imaging subject, adjusting one or more localizer scan parameters based on the anatomical ROI attribute map, and acquiring one or more localizer images of the anatomical ROI according to the one or more localizer scan parameters.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
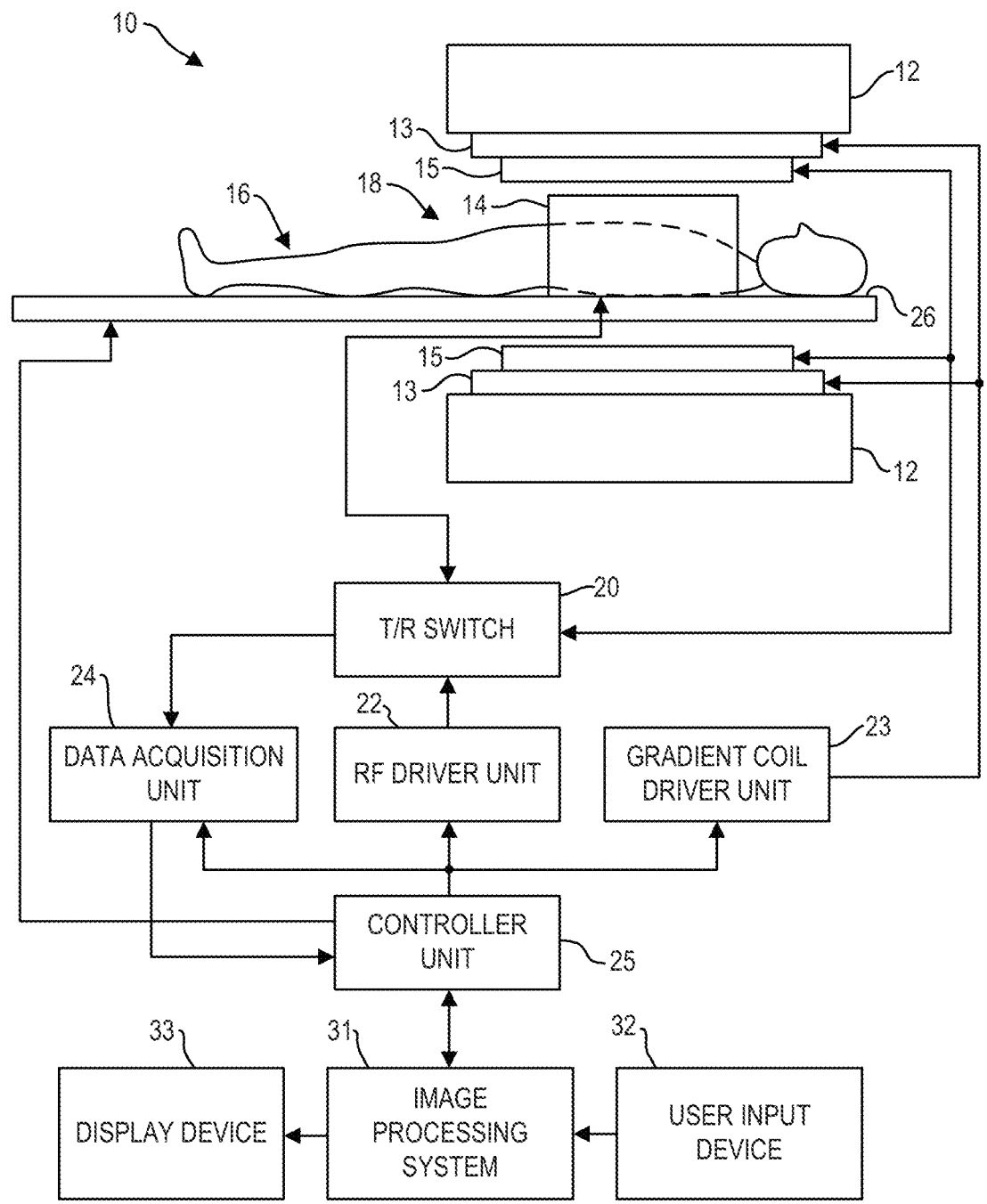
FIG. 1 shows a block diagram of an exemplary embodiment of an MRI system.

The drawings illustrate specific aspects of the described systems and methods for determining localizer scan settings from MR calibration images, using deep neural networks. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

The following description relates to various embodiments for determining attribute parameters of an anatomical region of interest (ROI), such as the location of a center point and an extent of the anatomical ROI to be imaged, orientation of the anatomical ROI to be imaged, and identification of the anatomical ROI to be imaged from magnetic resonance (MR) calibration images, which are typically very low resolution. The attribute parameters of the anatomical ROI may then be used to set localizer scan settings (e.g., the field of view of the localizer scan), which may result in more consistent localizer images and may reduce the need to perform multiple localizer scans, thereby lowering the scan time and producing more consistent, higher quality diagnostic images. In particular, certain anatomical regions, such as the shoulders, knees, ankles, spine, and other musculoskeletal regions, are relatively flexible/movable and/or positioned offset from a center of a patient's body. Accordingly, it may be difficult to position these anatomical regions in the center of the imaging bore, and thus the number of localizer rescans required when imaging these anatomical regions may be relatively high, which may lead to prolonged scan times, patient discomfort, and other issues. Further, because the localizer images are relied upon to establish certain parameters for the full diagnostic scan, low quality localizer images and/or improperly positioned anatomical ROIs in the localizer images may result in lower quality diagnostic images.

Thus, according to embodiments disclosed herein, the MR calibration images acquired before the localizer images may be used to determine attribute parameters of the anatomical ROI to be imaged in the localizer and diagnostic scans. The localizer scan parameters may be adjusted according to the attribute parameters determined from the calibration images, such that the anatomical ROI may be positioned properly in the localizer images. Moreover, in certain cases, the patient can be provided feedback based on the determined attribute parameters to alter anatomy position (e.g., move the knee, rotate the head etc.) to best suit the imaging parameters.

Figure 2:
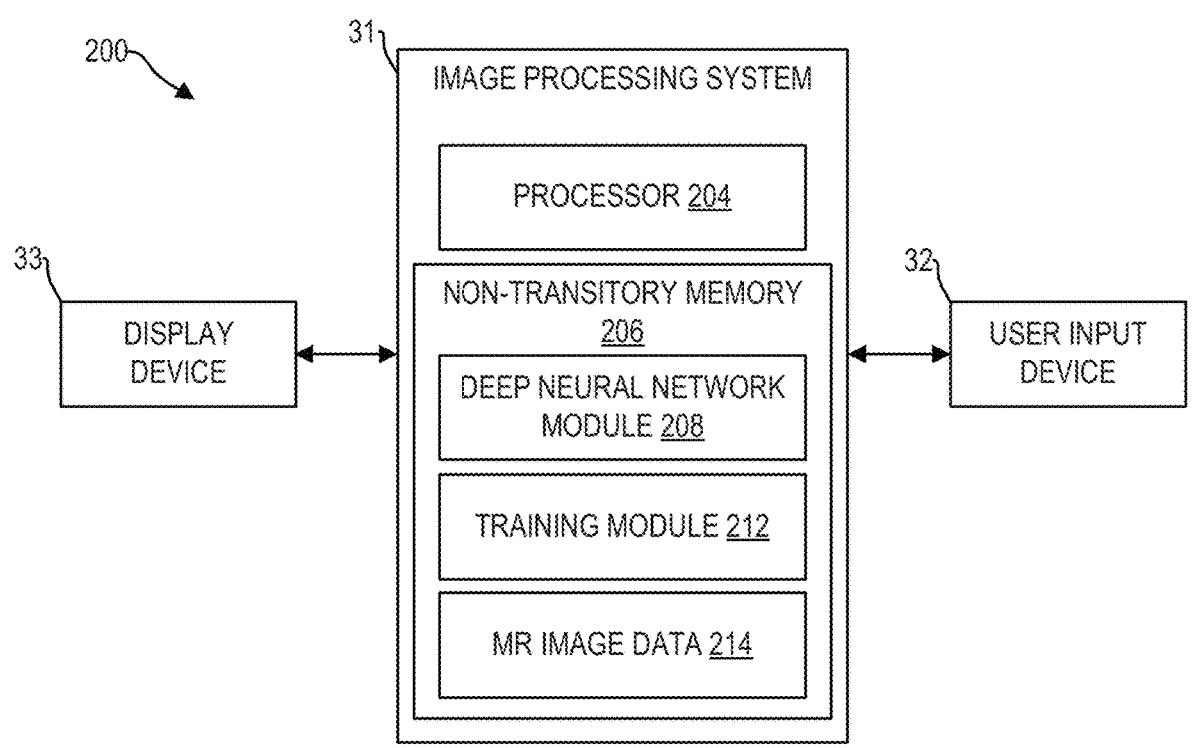
FIG. 2 is a schematic diagram illustrating a system for determining anatomical region of interest attribute parameters from an MR calibration image, according to an exemplary embodiment.
Figure 6:
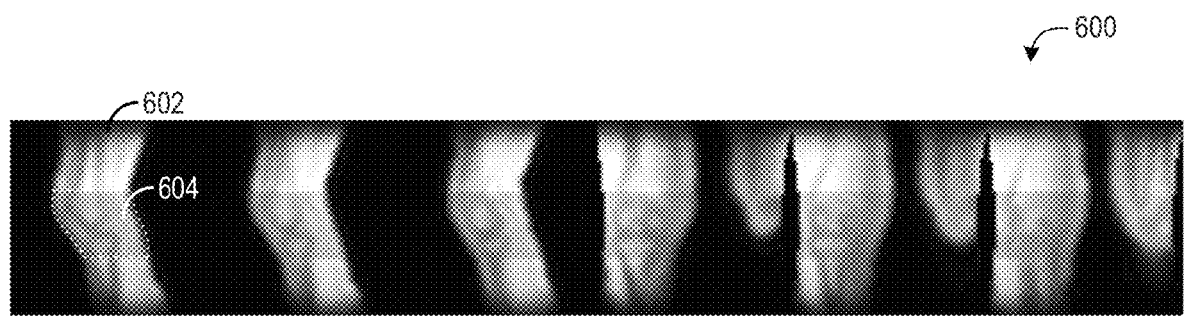
FIG. 6 shows example calibration images of an anatomical ROI and corresponding ground truth anatomical ROI attribute maps that may be used to train the deep neural network according to the method of FIG. 5.
Figure 7:
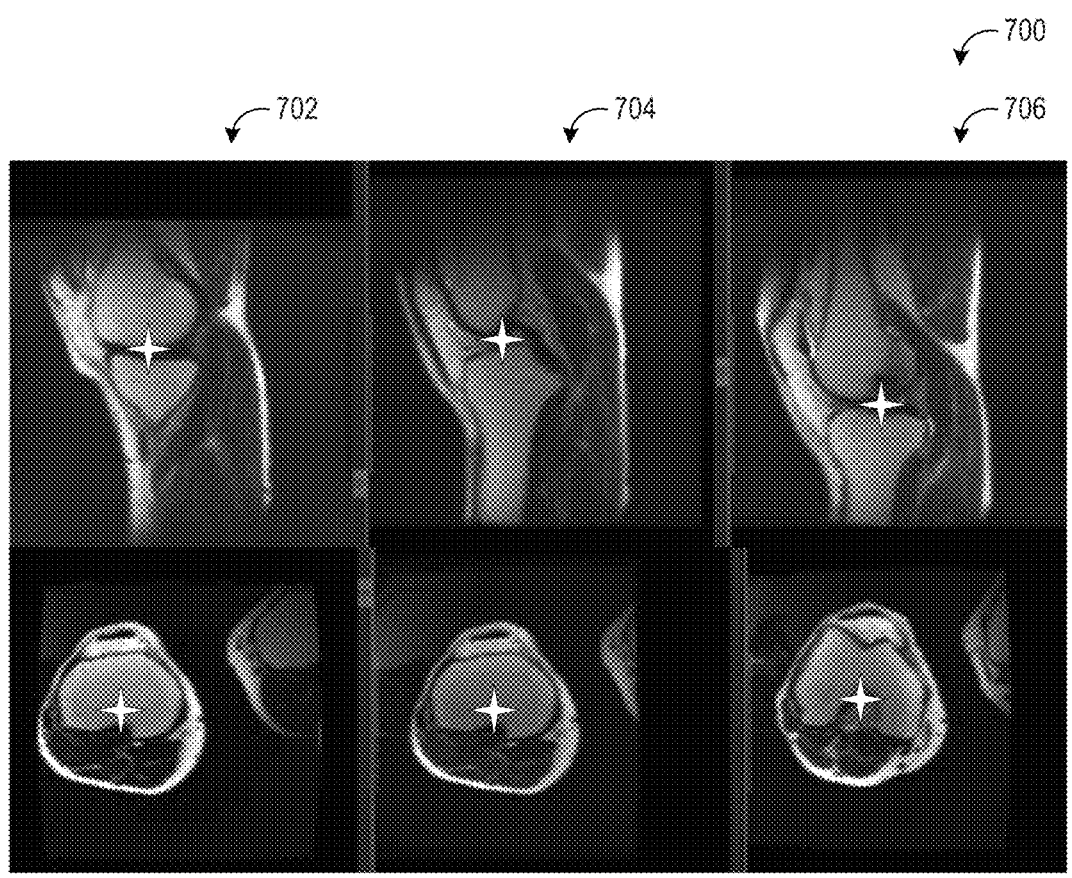
FIG. 7 shows example localizer images obtained without the automatically determined localizer scan settings described herein.
Figure 8:
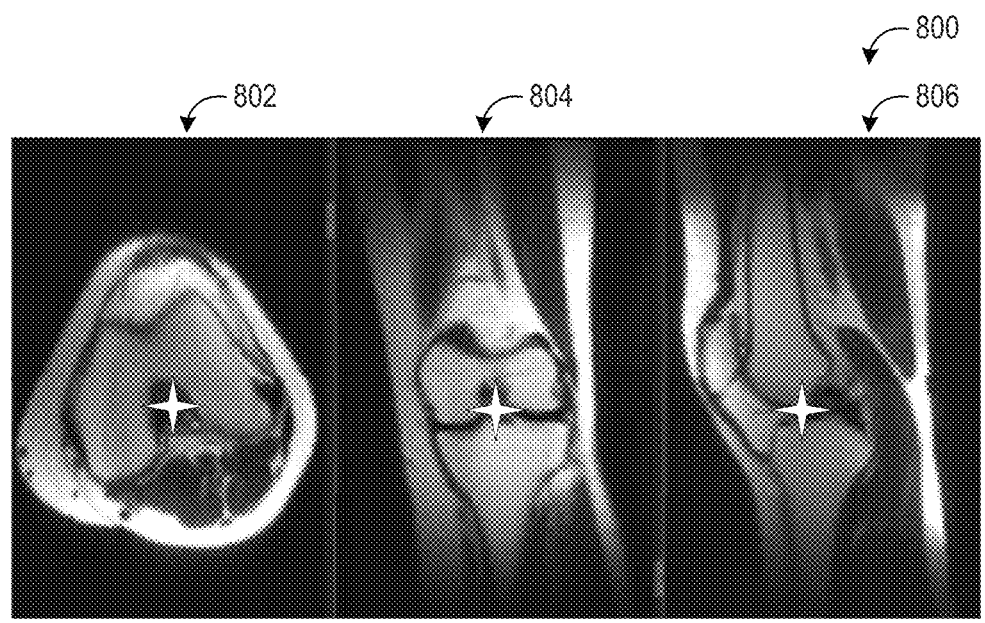
FIG. 8 shows example localizer images obtained with the automatically-determined localizer scan settings described herein, according to an exemplary embodiment.

In some embodiments, an MR calibration image acquired by an MRI system (such as the MRI system of FIG. 1) may be processed by an image processing system, such as the image processing system shown in FIG. 2. The image processing system may comprise a deep neural network stored in non-transitory memory, such as the deep neural network illustrated schematically in FIG. 3, which may be deployed to determine location parameters for an anatomical ROI and thus settings for a localizer scan based on the MR calibration image. The MRI system may execute a method for magnetic resonance imaging with the localizer images obtained according to the localizer scan settings determined from the MR calibration image, such as the method illustrated in FIG. 4. The deep neural network may be trained using, for example, a method illustrated in FIG. 5, which uses MR calibration images and corresponding anatomical ROI attribute maps, as shown in FIG. 6. The localizer scan settings determined according to embodiments of the current disclosure may be used to obtain localizer images, which may be then in turn be used to determine settings (e.g., a graphical prescription) for a diagnostic MRI scan. FIG. 7 and FIG. 8 show localizer images of a knee obtained without and with, respectively, the automatic determination of the attribute parameters of the anatomical ROI to determine the localizer scan settings.

MR calibration images are routinely acquired during MR calibration scans for use in selecting receive coil elements, measuring receive coil sensitivities to correct signal shadings, and/or accelerate data acquisition, prior to diagnostic imaging of patient anatomical regions. The current disclosure enables additional use to be made of calibration images, by accurately determining attribute parameters of an anatomical ROI to be scanned in a localizer scan from the calibration images, which enables more rapid acquisition of localizer images that include anatomical region(s) of interest in desired position(s), with fewer rescans. In some embodiments, the localizer images may include three plane localizer images (e.g., coronal, sagittal, axial) showing the full extent of the anatomy to be imaged in the subsequent diagnostic imaging scan. In some embodiments, the localizer images may be used by the MR system to automatically determine a prescription for the MR imaging scan, where high resolution MR images are obtained of the anatomical region(s) of interest for diagnostic medical purposes, for example. To ensure the automatic determination of the prescription is performed as desired, the anatomy to be imaged that is present in the localizer images (such as the knee) may be centered in the localizer images (e.g., a meniscus of the knee may be centered in all three planes of the localizer images).

In some embodiments, an MR calibration image may be used to determine corresponding anatomical ROI attribute parameters with a trained deep neural network. The deep neural network may be trained by using training data pairs, each pair including an MR calibration image and a corresponding anatomical ROI attribute map as ground truth reference. From an anatomical ROI attribute map, attribute parameters may be determined (e.g., which may include location parameters such as an anatomical center point and anatomical extent in the left-right and anterior-posterior planes, an orientation of the anatomical ROI, an identification/confirmation of the anatomy imaged in the calibration images). In order to increase the robustness of the deep neural network, training data may comprise MR calibration images and anatomical ROI attribute parameters measured at multiple anatomies to provide a wide variety of different anatomical ROIs in the training data set.

FIG. 1 illustrates an MRI system 10 that includes a magnetostatic field magnet unit 12, a gradient coil unit 13, an RF coil unit 14, an RF body or volume coil unit 15, a transmit/receive (T/R) switch 20, an RF driver unit 22, a gradient coil driver unit 23, a data acquisition unit 24, a controller unit 25, a patient table or bed 26, an image processing system 31, a user input device 32, and a display device 33. The RF coil unit 14 may be a surface coil or a volume coil, which is a local coil typically placed proximate to the anatomy of interest of a subject 16. Herein, the RF body coil unit 15 is a transmit coil that transmits RF signals, and the local RF coil unit 14 receives the MR signals. As such, the transmit body coil (e.g., RF body coil unit 15) and the receive coil (e.g., RF coil unit 14) are separate but electromagnetically coupled components. The MRI system 10 transmits electromagnetic pulse signals to the subject 16 placed in an imaging space 18 with a static magnetic field formed to perform a scan for obtaining magnetic resonance signals from the subject 16. One or more MR images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant primary magnetostatic field $B_0$.

The MRI system 10 also includes a gradient coil unit 13 that forms a gradient magnetic field in the imaging space 18 so as to provide the magnetic resonance signals received by the RF coil arrays with three-dimensional positional information. The gradient coil unit 13 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition.

The RF coil unit 14 is disposed, for example, to enclose the region to be imaged of the subject 16. In some examples, the RF coil unit 14 may be referred to as the receive coil. In the static magnetic field space or imaging space 18 where a static magnetic field $B_0$ is formed by the magnetostatic field magnet unit 12, the RF coil unit 15 transmits, based on a control signal from the controller unit 25, an RF pulse that is an electromagnet wave to the subject 16 and thereby generates a high-frequency magnetic field, $B_1$. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field $B_0$ produced by the magnetostatic field magnet unit 12 within the imaging space 18 to excite the nuclei. In contrast to the RF coil unit 14, which may be disconnected from the MRI system 10 and replaced with another RF coil unit, the RF body coil unit 15 is fixedly attached and connected to the MRI system 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coils (e.g., RF coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the image processing system 31.

The MRI system 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the system to carry out operations corresponding to pre-determined scanning. The recording medium may comprise, for example, a ROM, flexible disk, hard disk, optical disk, magneto-optical disk, CD-ROM, or non-transitory memory card. The controller unit 25 is connected to the user input device 32 and processes the operation signals input to the user input device 32 and furthermore controls the table 26, RF driver unit 22, gradient coil driver unit 23, and data acquisition unit 24 by outputting control signals to them. The controller unit 25 also controls, to obtain a desired image, the image processing system 31 and the display device 33 based on operation signals received from the user input device 32.

The user input device 32 includes user input devices such as a touchscreen, keyboard and a mouse. The user input device 32 is used by an operator, for example, to input such data as an imaging protocol and to set a region where an imaging sequence is to be executed. The data about the imaging protocol and the imaging sequence execution region are output to the controller unit 25.

The image processing system 31 includes a processor and non-transitory memory on which machine executable instructions may be stored, wherein the machine executable instructions may enable the processor to execute one or more of the steps of one or more of the methods herein disclosed. The image processing system 31 may be connected to the controller unit 25 and may perform data processing based on control signals received from the controller unit 25 or user input device 32. The image processing system 31 is also connected to the data acquisition unit 24 and generates spectrum data by applying various image processing operations to the magnetic resonance signals output from the data acquisition unit 24.

The image processing system 31 may determine localizer scan settings (e.g., localizer field of view) based on the location of a target anatomical region to be imaged (e.g., the location relative to the isocenter of the bore of the MR imaging system), which may be determined from MR calibration images acquired by MRI system 10. MRI system 10 may acquire localizer images according to the localizer scan settings, and the localizer images may then be used to determine scan parameters for acquiring diagnostic MR images, and/or the imaging processing system 31 may use the location of the anatomical ROI to notify an operator of the MR system to manually adjust one or more localizer scan settings, such as RF coil position. In one example, image processing system 31 and MRI system 10 may execute such a method, which will be discussed in detail below with reference to FIG. 4. Image processing system 31 may thereby determine localizer scan settings using rapidly acquired MR calibration images. Image processing system 31 may be further configured to display the localizer images acquired according to the automatically determined localizer scan settings via display device 33.

The display device 33 displays an image on the display screen of the display device based on control signals received from the controller unit 25. The display device 33 displays, for example, a localizer image and/or subsequent diagnostic MR images produced by the image processing system 31. Display device 33 may comprise a graphical user interface, wherein a user may interact with/input/alter one or more data fields via user input device 32. The display device 33 may display a two-dimensional (2D) slice image or three-dimensional (3D) image of the subject 16 generated by the image processing system 31.

During a scan, RF coil array interfacing cables (not shown in FIG. 1) may be used to transmit signals between the RF coils (e.g., RF coil unit 14 and RF body coil unit 15) and other aspects of the processing system (e.g., data acquisition unit 24, controller unit 25, and so on), for example to control the RF coils and/or to receive information from the RF coils. As explained previously, the RF body coil unit 15 is a transmit coil that transmits RF signals, and the local RF coil unit 14 receives the MR signals. More generally, RF coils are used to transmit RF excitation signals ("transmit coil"), and to receive the MR signals emitted by an imaging subject ("receive coil"). In some embodiments, the transmit and receive coils are a single mechanical and electrical structure or array of structures, with transmit/receive mode switchable by auxiliary circuitry. In other examples, the transmit body coil (e.g., RF body coil unit 15) and the surface receive coil (e.g., RF coil unit 14) may comprise separate components.

Referring to FIG. 2, MR image processing system 200 is shown, in accordance with an exemplary embodiment. In some embodiments, MR image processing system 200 is incorporated into the MRI system. In some embodiments, at least a portion of MR image processing 200 is disposed at a device (e.g., edge device, server, etc.) communicably coupled to the MRI system via wired and/or wireless connections. In some embodiments, at least a portion of MR image processing system 200 is disposed at a separate device (e.g., a workstation) which can receive images from the MRI system or from a storage device which stores the images generated by the MRI system. MR image processing system 200 may comprise image processing system 31, user input device 32, and display device 33.

Image processing system 31 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store deep neural network module 208, training module 212, and MR image data 214. Deep neural network module 208 may include one or more deep neural networks, comprising a plurality of weights and biases, activation functions, loss functions, gradient descent algorithms, and instructions for implementing the one or more deep neural networks to receive MR calibration images and map the input MR calibration images to output, wherein the output may be used to determine localizer scan settings for obtaining localizer images of anatomical regions corresponding to anatomical regions in the MR calibration image. For example, deep neural network module 208 may store instructions for implementing a neural network, such as the convolutional neural network (CNN) of CNN architecture 300, shown in FIG. 3. However, other architectures such as combination of fully connected networks and CNNs or generative adversarial networks and their variants can be used as well. Deep neural network module 208 may include trained and/or untrained neural networks and may further include various data, such as training data, training routines, or parameters (e.g., weights and biases), associated with one or more neural network models stored therein.

Non-transitory memory 206 may further include training module 212, which comprises instructions for training one or more of the deep neural networks stored in deep neural network module 208. Training module 212 may include instructions that, when executed by processor 204, cause image processing system 31 to conduct one or more of the steps of method 500, discussed in more detail below. In one example, training module 212 includes instructions for receiving training data pairs from MR image data 214, which comprise pairs of MR calibration images and corresponding ground truth anatomical ROI attribute maps, for use in training one or more of the deep neural networks stored in deep neural network module 208. In some embodiments, the training module 212 is not disposed at the image processing system 31. The deep neural network module 208 includes trained and validated network(s).

Non-transitory memory 206 may further store MR image data 214, such as MR images captured by the MRI system. For example, the MR image data 214 may include MR calibration images, annotated MR calibration images, localizer images, annotated localizer images, etc. In some embodiments, MR calibration images and corresponding ground truth anatomical ROI attribute maps along with embedded attributes (e.g. left or right knee or different brain regions, region with metal or not, orientation of the anatomy, etc.) may be stored in an ordered format, such that each MR calibration image of an anatomical region of a subject is associated with a ground truth anatomical ROI attribute map and the attributes of the same anatomical region of the same subject. Effectively, the ground-truth anatomical ROI attribute map may be a mask on top of the calibration scan images discerning between background (no anatomy) and foreground (the anatomy of interest), where this ground-truth mask may be obtained from previously acquired MR calibration image and localizer images, where the localizer scan is performed at the correct place and may be used to stipulate the ground-truth mask on the calibration scan.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

Image processing system 200 may further include user input device 32. User input device 32 may comprise one or more of a touchscreen, a keyboard, a mouse, a trackpad, a motion sensing camera, or other device configured to enable a user to interact with and manipulate data within image processing system 31.

Display device 33 may include one or more display devices utilizing virtually any type of technology. In some embodiments, display device 33 may comprise a computer monitor, and may display unprocessed and processed MR images. Display device 33 may be combined with processor 204, non-transitory memory 206, and/or user input device 32 in a shared enclosure, or may be peripheral display devices and may comprise a monitor, touchscreen, projector, or other display device known in the art, which may enable a user to view MR images produced by an MRI system, and/or interact with various data stored in non-transitory memory 206.

It should be understood that image processing system 200 shown in FIG. 2 is for illustration, not for limitation. Another appropriate image processing system may include more, fewer, or different components.

Figure 3:
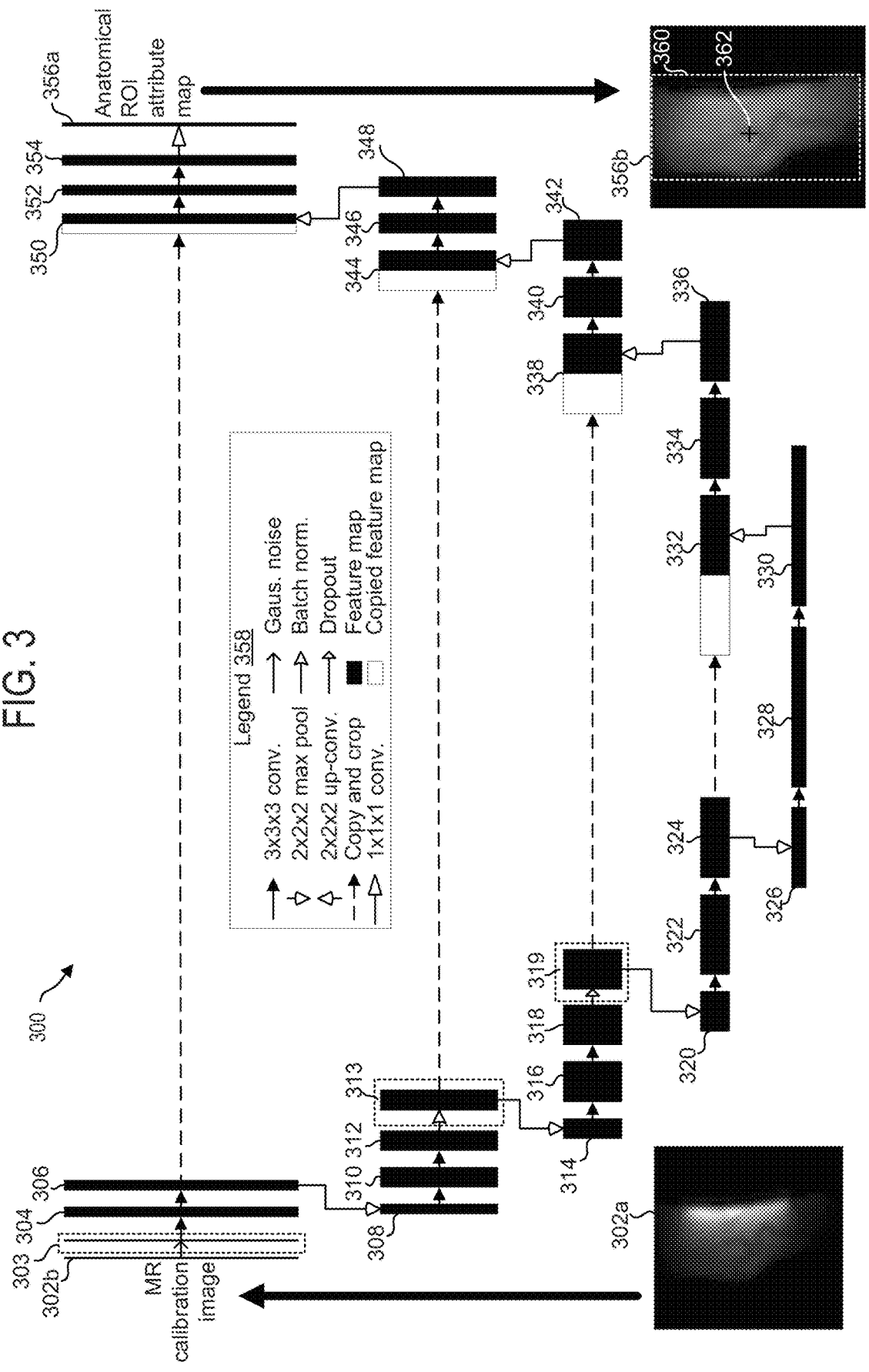
FIG. 3 is a schematic diagram illustrating the layout of a deep neural network which can be used in the system of FIG. 2, according to an exemplary embodiment.

Turning to FIG. 3, CNN architecture 300 for determining anatomical ROI attribute parameters, which may be used to determine localizer scan settings, from MR calibration images is shown, in accordance with an exemplary embodiment. In the description of FIG. 3, the anatomical ROI attribute parameters that are output from the CNN architecture may be referred to as an anatomical ROI attribute map, which may take on the form of a binary mask or multi-class, multi-labeled mask that may be superimposed on an input MR calibration image to define the location and/or other attributes of the anatomical ROI (e.g., the boundaries of the anatomical ROI in at least three planes and the center point of the anatomical ROI in the at least three planes) within the imaging field of view (FOV) used to obtain the MR calibration image. CNN architecture 300 represents a U-net architecture, which may be divided into an autoencoder portion (descending portion, elements 302b-330) and an autodecoder portion (ascending portion, elements 332-356a). CNN architecture 300 is configured to receive an MR calibration image/volume of an anatomical region, comprising a plurality of voxels, and map the input MR calibration image to an anatomical ROI attribute map of the same anatomical region. CNN architecture 300 includes a series of mappings, from an input image volume 302b which may be received by an input layer, through a plurality of feature maps, and finally to an output anatomical ROI attribute map 356b, which may be produced by an output layer 356a.

The various elements comprising CNN architecture 300 are labeled in legend 358. As indicated by legend 358, CNN architecture 300 includes a plurality of feature maps (and/or copied feature maps), wherein each feature map may receive input from either an external file, or a previous feature map, and may transform/map the received input to output to produce a next feature map. Each feature map may comprise a plurality of neurons, where in some embodiments, each neuron may receive input from a subset of neurons of a previous layer/feature map, and may compute a single output based on the received inputs, wherein the output may be propagated to a subset of the neurons in a next layer/feature map. A feature map may be described using spatial dimensions, such as length, width, depth, and hyper depth (which may correspond to features of each of voxel of the input image/volume), wherein the dimensions refer to the number of neurons comprising the feature map (e.g., the number of neurons along a length, the number of neurons along a width, the number of neurons along a depth, and the number of neurons along a hyper depth of a specified feature map).

In some embodiments, the neurons of the feature maps may compute an output by performing a dot product of received inputs using a set of learned weights (each set of learned weights may herein be referred to as a filter), wherein each received input has a unique corresponding learned weight, wherein the learned weight was learned during training of the CNN.

The transformations/mappings performed by each feature map are indicated by arrows, wherein each type of arrow corresponds to a distinct transformation, as indicated by legend 358. Rightward pointing solid black arrows indicate 3×3×3 convolutions with stride of one, wherein output from a 3×3×3 grid of feature channels of an immediately preceding feature map are mapped to a single feature channel of a current feature map. Each 3×3×3 convolution may be followed by an activation function, wherein, in one embodiment, the activation function comprises a rectified linear unit (ReLU).

Downward pointing hollow arrows indicate 2×2×2 max pooling, wherein the max value from a 2×2×2 grid of feature channels is propagated from an immediately preceding feature map to a single feature channel of a current feature map, thereby resulting in an 8-fold reduction in spatial resolution of the immediately preceding feature map. In some examples, this pooling occurs for each feature independently.

Upward pointing hollow arrows indicate 2×2×2 up-convolutions, which comprise mapping output from a single feature channel of an immediately preceding feature map to a 2×2×2 grid of feature channels in a current feature map, thereby increasing the spatial resolution of the immediately preceding feature map 8-fold.

Rightward pointing dash-tailed arrows indicate copying and cropping of a feature map for concatenation with another, later occurring, feature map. Cropping enables the dimensions of the copied feature map to match the dimensions of the feature map with which the copied feature map is to be concatenated. It will be appreciated that when the size of the first feature map being copied and the size of the second feature map to be concatenated with the first feature map are equal, no cropping may be performed.

Rightward pointing arrows with hollow elongated triangular heads indicate a 1×1×1 convolution, in which each feature channel in an immediately preceding feature map is mapped to a single feature channel of a current feature map, or in other words, wherein a 1-to-1 mapping of feature channels between an immediately preceding feature map and a current feature map occurs.

Rightward pointing arrows with chevron heads indicate incorporation of Gaussian noise into a received input feature map.

Rightward pointing arrows with arcuate hollow heads indicate batch normalization operations, wherein a distribution of activations of an input feature map are normalized.

Rightward pointing arrows with a short hollow triangular head indicates a dropout operation, wherein random or pseudo-random dropout of input neurons (as well as their inputs and outputs) occurs during training.

In addition to the operations indicated by the arrows within legend 358, CNN architecture 300 includes solid filled rectangles corresponding to feature maps, wherein feature maps comprise a height (top to bottom length as shown in FIG. 3, corresponds to a y spatial dimension in an x-y plane), width (not shown in FIG. 3, assumed equal in magnitude to height, corresponds to an x spatial dimension in an x-y plane), and depth (a left-right length as shown in FIG. 3, corresponds to the number of features within each feature channel). Likewise, CNN architecture 300 includes hollow (unfilled) rectangles, corresponding to copied and cropped feature maps, wherein copied feature maps comprise height (top to bottom length as shown in FIG. 3, corresponds to a y spatial dimension in an x-y plane), width (not shown in FIG. 3, assumed equal in magnitude to height, corresponds to an x spatial dimension in an x-y plane), and depth (a length from a left side to a right side as shown in FIG. 3, corresponds to the number of features within each feature channel).

Starting at input image volume 302b (herein also referred to as an input layer), data corresponding to an MR calibration image, such as that shown by MR calibration image 302a, may be input and mapped to a first set of features. In some embodiments, the input data is acquired during a calibration scan that is carried out with a proton density based gradient echo sequence. In some embodiments, the input data is pre-processed (e.g., normalized) before being processed by the neural network. In some embodiments, the input data is magnitude data.

Output layer 356a may comprise an output layer of neurons, wherein each neuron may correspond to a pixel of an anatomical ROI attribute map, and wherein output of each neuron may correspond to a predicted anatomical feature (or lack of the anatomical feature) in a given location within the input MR calibration image. For example, the output of a neuron may indicate whether the corresponding pixel of the anatomical ROI attribute map is part of a knee or is not part of a knee.

As shown in FIG. 3, the anatomical ROI attribute map 356b may illustrate the anatomical ROI. The extent of the anatomical ROI is a 3D oriented volume inside the calibration scan volume, wherein any two axes, either left-right or superior-inferior or anterior-posterior axis, may be used to set the localizer scan parameters. The anatomical ROI is captured by a 3D bounding box 360, which is formed by the boundary separating the foreground (the anatomy of interest) from the background (no anatomy) in the anatomical ROI attribute map 356b. Further, the anatomical ROI attribute map 356b may include a center point 362 that may define the center of the anatomical ROI, and may include the orientation of the anatomical ROI. While FIG. 3 shows the bounding box 360 and center point 362 as visual elements positioned on a viewable anatomical ROI attribute map, it is to be understood that the anatomical ROI attribute map, the bounding box, and/or the center point may be defined as coordinates in a coordinate system of the imaging bore, for example.

In this way, CNN architecture 300 may enable mapping of an MR calibration image to a predicted anatomical ROI attribute map that includes the location and/or other attributes of the anatomical ROI. CNN architecture 300 illustrates the feature map transformations which occur as an input image volume is propagated through the neuron layers of the convolutional neural network, to produce the predicted anatomical ROI attribute map.

The weights (and biases) of the convolutional layers in the neural network 300 are learned during training, as will be discussed in more detail with reference to FIG. 5 below. Briefly, a loss function is defined to reflect the difference between the anatomical ROI attribute map output by the neural network 300 and a corresponding ground truth anatomical ROI attribute map. The loss may be back projected to the neural network to update the weights (and biases) of the convolutional layers. A plurality of training data pairs, comprising MR calibration images and corresponding ground truth anatomical ROI attribute maps, may be used to train the neural network 300.

It will be appreciated that the current disclosure encompasses neural network architectures comprising one or more regularization layers, including batch normalization layers, dropout layers, Gaussian noise layers, and other regularization layers known in the art of machine learning which may be used during training to mitigate overfitting and increase training efficiency while reducing training duration. Regularization layers are used during CNN training and deactivated or removed during post training implementation of the CNN. These layers may be interspersed between the layers/feature maps shown in FIG. 3, or may replace one or more of the shown layers/feature maps.

It should be understood that the architecture and configuration of CNN 300 shown in FIG. 3 is for illustration, not for limitation. Any appropriate neural network can be used herein for predicting anatomical ROI attribute maps from MR calibration images, such as ResNet, recurrent neural networks, General Regression Neural Network (GRNN), etc. One or more specific embodiments of the present disclosure are described above in order to provide a thorough understanding. These described embodiments are only examples of systems and methods for predicting anatomical ROI attribute maps from MR calibration images using a deep neural network. The skilled artisan will understand that specific details described in the embodiments can be modified when being placed into practice without deviating the spirit of the present disclosure.

As appreciated by the MR calibration image 302a, MR calibration images may exhibit large amounts of shading, which may make it difficult to obtain segmentation with classical methods. However, the deep neural network described herein is able to process the calibration images to determine the corresponding anatomical ROI attribute parameters. The resulting location/mask information can then be used to derive information related to anatomy location (left/right, centers, sufficient coverage/coil placement, etc.).

Figure 4:
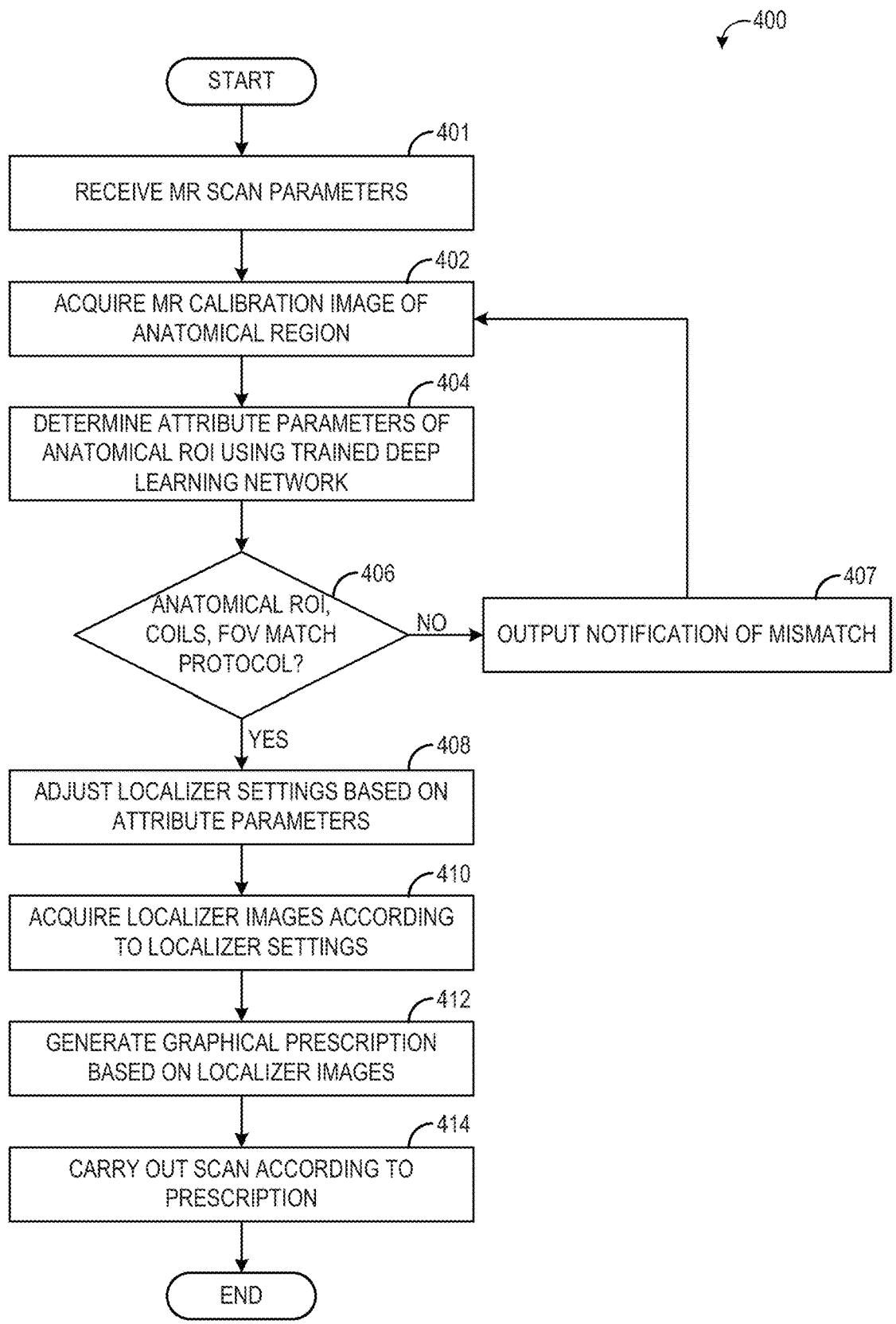
FIG. 4 is a flow chart illustrating a method for determining localizer scan settings based on an MR calibration image, according to an exemplary embodiment.

Referring to FIG. 4, a flow chart of a method 400 for acquiring magnetic resonance imaging localizer images according to MR system settings determined from an MR calibration image is shown, according to an exemplary embodiment. Method 400 may be implemented by the MRI system 10 shown in FIG. 1.

At 401, MR scan parameters are received. The MR scan parameters may be received via user input, such as by an operator of the MRI system selecting a scanning protocol displayed via a graphical user interface on a display device, for example. The MR scan parameters may include an anatomical ROI of an imaging subject (e.g., a patient) to be imaged during the diagnostic scan and, in some examples, a diagnostic goal of the diagnostic scan. For example, the MR scan parameters may include selection of a scanning protocol dictating that a diagnostic scan of a right knee of the imaging subject be carried out to diagnose presence or extent of an anterior cruciate ligament tear. The imaging subject may be positioned in the bore of the MRI system according to the scanning protocol (e.g., supine and feet first, such that the right knee is positioned in the imaging bore) and receive coils (e.g., knee coils) may be positioned on/around the anatomical ROI to be imaged.

At 402, an MR calibration image of an anatomical region (e.g., the anatomical ROI positioned in the imaging bore and on which the receive coils were placed) is acquired by the MRI system. The MR calibration image may be acquired by using, for example, a fast spin gradient echo sequence. In some embodiments, the MR calibration image may be a 3D volume. The MR calibration image or volume may include a relatively large FOV, such that the anatomical ROI is included in the calibration image and in some examples, with additional anatomical features. MR calibration images/volumes may be acquired/captured in relatively short amounts of time, as compared to diagnostic images. For example, an MR calibration image may be captured in under 3 seconds, using a fast spin gradient echo sequence with TR/TE of 1.4 ms/0.4 ms, receive bandwidth of 62.5 KHz, resolution of 32×32×28 on a 48 cm×48 cm×42 cm imaging volume. By utilizing MR calibration images, the acquisition/capture of which may already be incorporated in a diagnostic imaging workflow, as the basis of anatomical ROI location/attribute prediction and hence localizer scan settings, method 400 may enable acquisition of localizer images in less time, and with fewer scans, than current methods, which may require multiple rescans before the anatomical ROI is positioned in the localizer images at a desired location.

At 404, attribute parameters of the anatomical ROI are determined using a trained deep neural network. For example, the MR calibration image is input into a trained deep neural network, outputs an anatomical ROI attribute map using the calibration image as input. In some embodiments, the input MR calibration image is a magnitude image. In some embodiments, the input MR calibration image may be raw k-space data. In some embodiments, the deep neural network is a CNN, having an autoencoder-autodecoder type architecture, such as CNN 300 shown in FIG. 3. In some embodiments, each pixel/voxel value of the MR calibration image is input into a distinct node/neuron of the input layer of the deep neural network, and propagates through the one or more hidden layers, until reaching an output layer of the deep neural network. The relationship between two adjacent layers of the deep neural network, other than the input layer, may be described as follows:

$$Y_j = f\left(\sum_{i=1}^{n} W_{ji} X_i + B_j\right)$$

Where $X_i$ is the output of the i-th neuron of the preceding layer, $Y_j$ is the j-th neuron of the subsequent layer, $W_{ji}$ is the weight, and $B_j$ is the bias. In some embodiments, the activation function $f$ is a rectified linear unit (ReLU) function, for example, plain ReLU function, leaky ReLU function, parametric ReLU function, etc.

In some embodiments, the output from the output layer of the deep neural network is of the same dimension as the input MR calibration image. However, in some embodiments, the output may comprise a matrix of values with dimensions less than the dimensions of the input MR calibration image. In some embodiments, the output may comprise a matrix of values, with each value indicating whether or not a pixel/voxel captured in the MR calibration image belongs to the anatomical ROI dictated by the scanning parameters. The output of the deep neural network may include or be used to determine various attributes of the anatomical ROI, such as the location of a center point of the anatomical ROI and/or a bounding box defining an extent of the anatomical ROI in the localizer imaging space (which may be the same or different than the coordinates of the imaging bore).

At 406, method 400 includes determining if the anatomical ROI in the calibration image, the position of the receive RF coil(s), and the FOV of the calibration image match the anatomical ROI, position of the receive RF coil(s), and FOV indicated by the scanning protocol. For example, based on the output from the deep neural network (e.g., based on the location parameters of the anatomical ROI determined using the trained deep neural network), the center point of the anatomical ROI (e.g., the patella of the right knee) may be determined along each axis with respect to the FOV imaged in the calibration scan (e.g., along the superior-inferior axis, the anterior-posterior axis, and the left-right axis). If the center point is positioned more than a threshold distance from the center of the FOV, it may be determined that the FOV is not at a desired position and/or the receive RF coil(s) have been placed out of a target position (e.g., not centered over the knee) and thus a mismatch may be indicated. In another example, the output from the deep neural network may indicate which knee is currently being imaged (e.g., left or right). If the output indicates that the left knee is being imaged while the scanning protocol dictates that the right knee is the knee to be imaged, a mismatch may be indicated. If the anatomical ROI, FOV, and/or RF coil position do not match the scanning protocol, method 400 proceeds to 407 to output a notification of the mismatch. For example, a notification may be displayed on a graphical user interface displayed on a display device of the MRI system, which may be viewed by the operator of the MRI system. If the RF coil(s) are not positioned properly, a notification may be displayed alerting the operator that the RF coil(s) are not positioned properly. If the wrong anatomy is being imaged, a notification may be displayed alerting the operator that the wrong anatomy is being imaged. If the FOV is not set for optimal imaging, a notification may be output altering the operator to adjust the FOV by moving the table or by changing the center of FOV with software. Upon the notification of the mismatch being output, method 400 may return back to 402 to reacquire the MR calibration image to ensure the correct anatomical ROI is being imaged, the FOV is set as desired for optimal imaging, and/or the receive RF coils are properly positioned.

If the anatomical ROI, FOV, and/or RF coil position do match the scanning protocol, method 400 proceeds to 408 to adjust one or more localizer scan settings based on the attribute parameters determined at 404. As explained above with respect to FIG. 3, the attribute parameters may include the location of the center point and/or boundaries of the anatomical ROI in one or more imaging planes and/or with respect to the imaging bore and/or field of view (FOV) of the calibration images. The localizer scan settings may be adjusted so that the center point of the anatomical ROI is in the center of the localizer images. Localizer scan settings that may be adjusted based on the attribute parameters include the localizer FOV, direction of phase encode and readout lines in acquisition, number of phase-encode k-space lines, optimal number of slices for localizer coverage, slice thickness and gap settings, orientation of the localizer scan, a position of a table supporting the imaging subject within the bore of the MRI system (e.g., table 26 of FIG. 1), and/or a no phase wrap factor that controls the amount of phase oversampling to be performed during acquisition of the localizer images. The localizer scan settings may be adjusted automatically by the MRI system (e.g., adjusted according to instructions stored in memory of the MRI system and executed by a processor of the MRI system without explicit user input) and/or the localizer scan settings may be adjusted by an operator of the MRI system (e.g., the operator may manually adjust the table position and/or enter input selecting a desired FOV and/or no phase wrap factor). When the adjustments are performed by the operator, the operator may be notified of the attribute parameters. For example, the anatomical ROI attribute map may be output as an image on a display device.

At 410, localizer images are acquired according to the localizer settings determined/adjusted at 408. The localizer images may include 3-plane localizer images, where at least three localizer images are obtained with at least one localizer image in a respective plane of three anatomical planes of interest (e.g., coronal, axial, and sagittal). The localizer images may be acquired using a suitable MR protocol, such as a T1 weighted low resolution scan.

At 412, a graphical prescription is generated based on the localizer images. The graphical prescription may comprise graphical prescription marks such as points, lines, boxes, or other shapes overlaid on key frames of the localizer images to indicate a desired region of interest, as well as indicate the field of view, spacing, thickness, location, and orientation of the desired region of interest. In this way, the graphical prescription prescribes both volume orientation and volume coverage to ensure that the desired region of interest is accurately imaged during the full diagnostic scan. The graphical prescription may be generated based on user input, in some embodiments. For example, the localizer images may be displayed on the display device, and the operator of the MRI system may enter input (e.g., via touch input, a mouse, and/or a keyboard) indicating the location/orientation of the desired ROI for scanning and spacing and thickness of slices to be obtained during the full diagnostic scan. In some embodiments, the graphical prescription may be generated automatically by entering the localizer images into one or more trained deep neural networks. For example, the one or more deep neural networks have been trained to extract key features from the localizer images, identify anatomy and/or planes of each localizer image, and identify key frames of the localizer images. Using the key features, the anatomy and planes, and the key frames, the one or more trained deep neural networks may output the graphical prescription. Detailed methods and systems are described in U.S. patent application Ser. No. 16/052,427 filed Aug. 1, 2018 ("Systems and Methods for Automated Graphical Prescription with Deep Neural Networks") and U.S. patent application Ser. No. 16/051,723 filed Aug. 1, 2018 ("Plane Selection Using Localizer Images"), which are both incorporated herein in their entirety by reference.

At 414, the diagnostic scan is carried out according to the prescription. In some embodiments, an operator of the MRI system may first confirm that the key frames and the graphical prescription displayed via the display device accurately prescribe the coverage and orientation for the desired anatomical ROI to be scanned. In such examples, the operator may manually adjust the scanning protocol according to the graphical prescription. In some embodiments, the scanning protocol is automatically adjusted according to the graphical prescription, as operator intervention may be unnecessary if the accuracy of the neural network system is sufficient for ensuring that the desired region of interest will be correctly imaged with sufficient coverage. In either case, the diagnostic scan is performed according to the adjusted scanning protocol. The diagnostic scan may be carried out according to any appropriate pulse sequence (e.g., echo spin, gradient echo) and may be of any appropriate contrast (e.g., proton density weighted, T1-weighted, T2-weighted, etc.). Method 400 then returns.

In this way, method 400 enables rapid and accurate acquisition of localizer images by adjusting localizer scan settings according to anatomical ROI attribute parameters determined from an MR calibration image, reducing the likelihood that multiple localizer scans will have to be performed.

Figure 5:
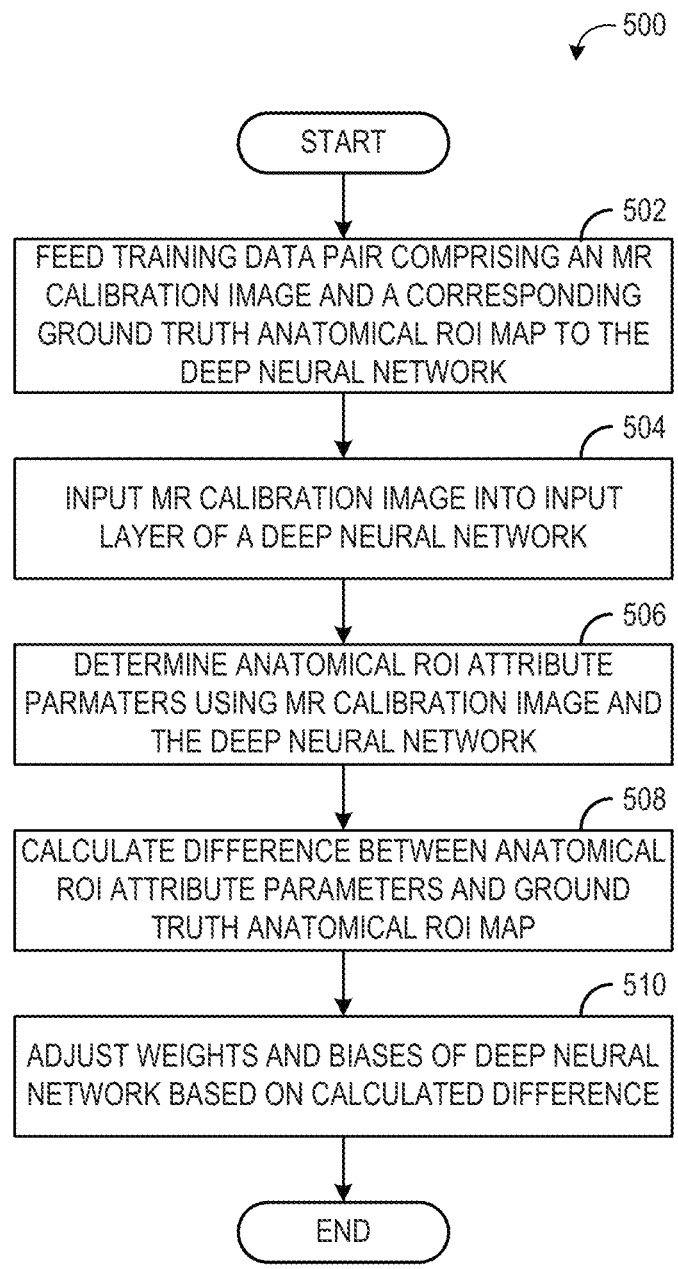
FIG. 5 is a flow chart illustrating a method for training a deep neural network to predict anatomical ROI attribute parameters from MR calibration images, according to an exemplary embodiment.

Referring to FIG. 5, a flow chart of a method 500 for training a deep neural network (such as CNN 300 shown in FIG. 3) is shown, according to an exemplary embodiment. Method 500 may be implemented by the system 10 shown in FIG. 1 or the system 200 shown in FIG. 2. In some embodiments, method 500 may be implemented by training module 212, stored in non-transitory memory 206 of image processing system 31.

At 502, a training data pair, from a plurality of training data pairs, is fed to a deep neural network, wherein the training data pair comprises an MR calibration image (which may be a 3D image, also referred to as a volume) and a corresponding ground truth anatomical ROI attribute map. In some embodiments, the training data pair, and the plurality of training data pairs, may be stored in the image processing system, such as in MR image data 214 of image processing system 31. In other embodiments, the training data pair may be acquired via communicative coupling between the image processing system and an external storage device, such as via Internet connection to a remote server. FIG. 6 shows example training data pairs 600 each including an MR calibration image 602 and a ground truth anatomical ROI attribute map 604. In the example shown in FIG. 6, each MR calibration image may include a large FOV, such that a knee is imaged, as well as regions of a leg above and below the knee. Each ground truth anatomical ROI attribute map may include a smaller FOV, such that only the anatomical ROI (e.g., the knee) is included in the ground truth anatomical ROI attribute map. In some embodiments, the ground truth anatomical ROI attribute map is obtained from the calibration image and corresponding localizer images, where the localizer scan is performed at the correct place and is used to stipulate the ground truth anatomical ROI attribute map on the calibration scan. The ground anatomical ROI attribute maps are shown as masks superimposed over the corresponding calibration images, but other depictions of the ground truth ROI are possible without departing from the scope of this disclosure. The ground-truth masks may be determined by the target of the MR exam, e.g., the mask may be any sub-region inside the calibration scan region including the anatomical ROI, which may be any anatomy of the human body present in the large FOV of the calibration scan. The goal of the ground-truth mask is to set a smaller FOV of the localizer scan including the target anatomy.

At 504, the MR calibration image of the training data pair is input into an input layer of the deep neural network. In some embodiments, the MR calibration image is input into an input layer of a CNN, having an autoencoder-autodecoder type architecture, such as CNN 300 shown in FIG. 3. In some embodiments, each voxel value of the MR calibration image is input into a distinct node/neuron of the input layer of the deep neural network.

At 506, anatomical ROI attribute parameters are determined using the MR calibration image and the deep neural network. For example, the deep neural network may map the input MR calibration image to anatomical ROI attribute parameters by propagating the input MR calibration image from the input layer, through one or more hidden layers, until reaching an output layer of the deep neural network. In some embodiments, the output of the deep neural network comprises a matrix of values, with each value corresponding to an identified anatomical feature at a respective voxel of the input MR calibration image. These values may take the form of an anatomical ROI attribute map, as explained above with respect to FIG. 3.

At 508, the difference between the anatomical ROI attribute parameters output by the deep neural network and the ground truth anatomical ROI attribute map corresponding to the calibration image is calculated by the image processing system. In some embodiments, a difference between each output value, corresponding a predicted anatomical feature of the input MR calibration image, and an anatomical feature indicated by the ground truth anatomical ROI attribute map is determined. The difference may be calculated according to a loss function, for example:

$$\text{DICE} = (S \cap T)/(S \cup T),$$

wherein S is the ground truth anatomical ROI attribute map and T is the predicted anatomical ROI attribute parameters (which may be in the form of a map similar to the ground truth anatomical ROI attribute map). In other words, the output of the deep neural network may include, for each voxel of the input MR calibration image, an indication of whether or not that pixel is part of the anatomical ROI (e.g., the knee). The ground truth anatomical ROI attribute map may likewise include an indication, for each pixel of the MR calibration image, whether or not that pixel is part of the anatomical ROI. The difference between each output value and the ground truth anatomical ROI attribute map may then be determined.

At 510, the weights and biases of the deep neural network are adjusted based on the difference calculated at 508. The difference (or loss), as determined by the loss function, may be back propagated through the neural learning network to update the weights (and biases) of the convolutional layers. In some embodiments, back propagation of the loss may occur according to a gradient descent algorithm, wherein a gradient of the loss function (a first derivative, or approximation of the first derivative) is determined for each weight and bias of the deep neural network. Each weight (and bias) of the deep neural network is then updated by adding the negative of the product of the gradient determined (or approximated) for the weight (or bias) with a predetermined step size. Method 500 may then end. It will be noted that method 500 may be repeated until the weights and biases of the deep neural network converge, or the rate of change of the weights and/or biases of the deep neural network for each iteration of method 500 are under a threshold.

In this way, method 500 enables a deep neural network to be trained to predict the location and/or other attributes (e.g., identification) of an anatomical ROI from an MR calibration image, thereby facilitating automatic determination of a FOV for a subsequent localizer scan.

Turning to FIG. 7, an example set of localizer images 700 are shown. The set of localizer images 700 shown in FIG. 7 were obtained according to conventional methods, where an operator sets the localizer scan settings (e.g., FOV) based on a prediction of where the anatomical ROI (herein, a knee) is located relative to the center of the imaging bore. The set of localizer images 700 includes three subsets of localizer images, a first subset 702, a second subset 704, and a third subset 706. The first subset 702 may be a set of localizer images obtained during an initial localizer scan. In the first subset 702 of localizer images, a center point of the knee (shown by the star in each of the images) is offset from the center of each of the localizer images of the first subset 702. Thus, the operator may choose to reposition the knee of the imaging subject in an attempt to obtain higher quality localizer images. The second subset 704 may be a second set of localizer images obtained during a second localizer scan performed after the initial localizer scan. Again, the center of the knee is not centered in the center of the localizer images in the second subset 704 of localizer images. Thus, the operator may choose to again reposition the knee of the imaging subject in an attempt to obtain higher quality localizer images. The third subset 706 may be a third set of localizer images obtained during a third localizer scan performed after the second localizer scan. While the center of the knee is not centered in the center of the localizer images in the third subset 706 of localizer images, the operator may decide to utilize the third subset 706 of localizer images for determining the prescription of the subsequent diagnostic scan, which may result in less than full coverage of the anatomical ROI in the diagnostic scan and/or other issues, such as imaging artifacts. In addition to the issue of repositioning and rescanning to obtain high-quality localizer images, low-quality localizer images (e.g., where the target anatomy is not properly centered in the images) may affect both the localizer images and the final high-resolution images due to the intrinsic problem of manually centering an object in a 3D space. This increases the complexity of any further automated solutions for plane prescription. Additionally, scan orientation of the anatomical image may not be optimal resulting in images that may not clearly show all anatomical details, which may result in mis-diagnosis of a patient condition. Overall, this can also result in the patient needing to be recalled for another scan.

FIG. 8 shows an example set of localizer images 800 obtained according to the embodiments described herein, where the localizer scan FOV is automatically determined based on the predicted location of the anatomical ROI determined from an MR calibration image. The set of localizer images 800 includes a first localizer image 802, a second localizer image 804, and a third localizer image 806. As appreciated in FIG. 8, the center of the anatomical ROI (the knee) is centered in each of the images (shown by the star). By automatically setting the FOV based on the predicted location of the anatomical ROI, consistent, high-quality localizer images may be obtained in a single localizer scan.

Thus, the embodiments disclosed herein may reduce the acquisition of localizer images that are not suitable for downstream diagnostic scan planning. For example, improper localizer images may include imaging artifacts (e.g. aliasing, wrap-arounds, or missing structures), which subsequently impact the downstream pipe-line which use the localizer images to generate the scan planes; either manually or automatically. This problem is acute when scanning features of the musculoskeletal system (e.g., knee, shoulder, or ankle) and spine regions where localizer scans are often repeated (e.g., localizer scans may be repeated in 30-50% of these types of scans). As disclosed herein, the calibration images may be used to determine the anatomical characteristics based on scan protocol requirements to ensure that localizer scans (or any additional scans) are correctly positioned (e.g., in the case of knee scans, right vs left knee or locate the anterior-posterior and left-right landmarks and coil shift along superior-inferior). Calibration images are part of routine clinical protocol and are used to calibrate different imaging parameters for each patient's scans. The calibration images are characterized by extremely low resolution and have large intensity variations across the FOV due to RF coil related shading, which lack detailed anatomical information. To obviate these challenges or avoid additional processing to remove these artifacts, a learning-based neural network is deployed to analyze and locate these landmark characteristics with poorer quality calibration scans. Further, this approach does not increase the total scan time as calibration scans are always part of pre-scan in routine clinical exams.

The gross anatomy location (also referred to herein as the anatomical ROI location) determined from the calibration images may be used for scan plane planning in terms of correctly positioned localizers for further processing; either manually or automatically. This will help reduce the rate of localizer rescan from current 33% to 0%. In some examples, an operator of the MRI system may be warned in case there is a mismatch between the scanning protocol and the scanning set-up (e.g., the protocol is setup for a right knee and the RF coils are wrapped on left knee, etc.) or warned as to the correct RF coil placement (e.g., move the RF coil by 5 cm superior to get best coverage, etc.) or FOV placement (e.g., move spine FOV along A-P by 3 cm posterior to get spine coverage for coronal and sagittal coverage).

Further, the region of interest coverage (e.g., background vs. foreground) may be determined based on the gross anatomy location as determined from the calibration images and used to adjust the no phase wrap factor to avoid phase wraps, the patient table may be moved to bring the organ of interest to the MRI imaging bore isocenter (for full body scan with body coils), and so forth.

Further still, the scanning protocol may be customized based on scan requirement and the anatomical ROI location determined from the calibration images. This may include automatically populating the localizer orientations (sagittal/axial/coronal) with proper number of slices, mm thickness, slice gap and orientation for the landmark to be prescribed. For example, in the case of a knee, if only the meniscus plane is desired, it may suffice to acquire only sagittal/coronal data around the center points determined from the calibration images and an axial localizer scan may not be even be conducted.

In some examples, the localizer images may be used in an automated plane prescription workflow for MRI which utilizes clinically available three plane localizers to determine the scan planes for the full diagnostic scan using a cascade of neural networks. In MRI scanning of free-form extremities (lower and upper) such as knee, shoulder, ankle or spine, the initial localizer set-up required for scan planning is completely blinded to the MRI technician. Since the anatomy is away from isocenter and patient extremity locations differ substantially, the MRI technician needs to account for shifts between the anatomy and scanner center line, etc. Consequently, based on the training and experience of the MRI technician, this can result in significant re-takes of the localizer data, before the suitable localizer is scanned. This results in significant lag in overall scanning workflow, variability in the scan plane prescription, and consequently affects the quality of the clinical MRI data generated. If the localizer data obtained by un-trained technician has artifacts such as image wrap or image cropping landmark of interest, then it also increases the complexity of automated scan plane prescription algorithms or necessitates additional processing steps, thereby increasing computation time to obtain accurate result.

Using the calibration data along with learning-based algorithms described herein, the correct localization of the gross anatomy may be determined, the operator of the MRI system may be warned if set-up is incomplete and/or the set-up of the scan may be automatically adjusted (in cases where the problem can be solved by moving the table or FOV placement with software, etc.), and consistent scan plane prescription may be provided, regardless of technician training and experience. Providing consistency in localizers helps reduce wasted scan time, reduce the overall complexity of learning architectures and post processing schemes.

The technical effect of determining localizer scan settings from an anatomical ROI attribute map obtained from a calibration image using a deep neural network is consistent, higher quality localizer images and reduced incidence of rescans.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for magnetic resonance imaging (MRI), the method comprising:
  acquiring a magnetic resonance (MR) calibration image of an imaging subject with an MRI system;
  mapping, by a trained deep neural network, the MR calibration image to a corresponding anatomical region of interest (ROI) attribute map for an anatomical ROI of the imaging subject, the anatomical ROI attribute map defining attributes of the anatomical ROI within a set field of view (FOV) used to obtain the MR calibration image;
  adjusting one or more localizer scan parameters based on the anatomical ROI attribute map; and
  acquiring, with the MRI system, one or more localizer images of the anatomical ROI according to the one or more localizer scan parameters.

2. A method, comprising:
  training a deep neural network to map magnetic resonance (MR) calibration images to corresponding anatomical region of interest (ROI) attribute maps, wherein the training includes:
    feeding a plurality of training data pairs to the deep neural network, wherein each training data pair includes an MR calibration image and a corresponding ground truth anatomical ROI attribute map with embedded attribute parameters;
    correlating the MR calibration image in a training data pair to a predicted anatomical ROI attribute map using the deep neural network;
    calculating a difference between the predicted anatomical ROI attribute map and the ground truth anatomical ROI attribute map; and
    adjusting parameters of the deep neural network via backpropagation based on the difference between the predicted anatomical ROI attribute map and the ground truth anatomical ROI attribute map;
  receiving a particular MR calibration image; and
  determining, from the particular MR calibration image, a corresponding anatomical ROI attribute map using the trained deep neural network.

3. A magnetic resonance imaging (MRI) system, comprising:
  a memory storing a trained deep neural network and instructions; and
  a processor communicably coupled to the memory and when executing the instructions, configured to:

instruct the MRI system to acquire an MR calibration image of an imaging subject;

determine, with the MR calibration image and using the trained deep neural network, an anatomical region of interest (ROI) attribute map, the anatomical ROI attribute map defining one or more attribute parameters of an anatomical ROI of the imaging subject, the one or more attribute parameters comprising one or more of a center point and/or extent of the anatomical ROI within an imaging bore of the MRI system, an orientation of the anatomical ROI, and an identification of the anatomical ROI;

determine one or more localizer scan settings for a localizer scan of the anatomical ROI based on the anatomical ROI attribute map; and instruct the MRI system to acquire a localizer image using the one or more localizer scan settings.

4. The method of claim 1, further comprising:

generating a graphical prescription using the localizer images; and performing a diagnostic scan of the anatomical ROI of the imaging subject with the MRI system according to the graphical prescription, and wherein the MR calibration image is acquired with a first MR protocol and the one or more localizer images are acquired with a second, different MR protocol.

5. The method of claim 1, wherein adjusting the one or more localizer scan parameters comprises adjusting a localizer FOV, and wherein acquiring the one or more localizer images comprises acquiring the one or more localizer images with the adjusted localizer FOV, wherein the localizer FOV is smaller than the set FOV.

6. The method of claim 1, wherein adjusting the one or more localizer scan parameters comprises adjusting a location of a table supporting the imaging subject within an imaging bore of the MRI system, and wherein acquiring the one or more localizer images comprises acquiring the one or more localizer images with the table at the adjusted position.

7. The method of claim 1, wherein adjusting the one or more localizer scan parameters comprises adjusting a no phase wrap factor, and wherein acquiring the one or more localizer images comprises acquiring the one or more localizer images with the adjusted no phase wrap factor.

8. The method of claim 1, wherein adjusting the one or more localizer scan parameters comprises adjusting one or more of a number of slices, slice thickness, slice gap, orientation, and number of lines of k-space, and wherein acquiring the one or more localizer images comprises acquiring the one or more localizer images with the adjusted number of slices, slice thickness, slice gap, orientation, and/or number of lines of k-space.

9. The method of claim 1, further comprising determining one or more attribute parameters based on the anatomical ROI attribute map, wherein the one or more attribute parameters comprise one or more of a center point and/or extent of the anatomical ROI, an orientation of the anatomical ROI, and an identification of the anatomical ROI, and wherein adjusting one or more localizer scan parameters comprises adjusting one or more localizer scan parameters based on the one or more attribute parameters.

10. The method of claim 1, wherein the anatomical ROI is determined based on a scanning protocol selected by a user.

11. The method of claim 10, further comprising determining, based on the anatomical ROI attribute map, whether the anatomical ROI matches an anatomical ROI specified by the scanning protocol, and if the anatomical ROI determined does not match the anatomical ROI specified by the scanning protocol, outputting a notification alerting an operator that the anatomical ROI does not match the anatomical ROI specified by the scanning protocol.

12. The method of claim 10, further comprising determining, based on the anatomical ROI attribute map, whether a receive radio frequency (RF) coil is positioned at a target position, and if the receive RF coil is not positioned at the target position, outputting a notification alerting an operator of the MRI system that the receive RF coil is not positioned at the target position.

13. The method of claim 10, further comprising determining, based on the anatomical ROI attribute map, whether the set FOV of the MR calibration image matches a target FOV specified by the scanning protocol, and if the set FOV does not match the target FOV, outputting a notification alerting an operator that the set FOV does not match the target FOV.

14. The method of claim 2, wherein the anatomical ROI attribute map includes one or more of a center point and/or extent of the anatomical ROI within an imaging bore of the MRI system, an orientation of the anatomical ROI, and an identification of the anatomical ROI.

15. The MRI system of claim 3, wherein the memory further stores instructions for training the deep neural network.

16. The MRI system of claim 15, wherein the processor, when executing the instructions for training the deep neural network, is configured to:

feed a plurality of training data pairs to the deep neural network, each training data pair includes an MR calibration image and a corresponding ground truth anatomical ROI attribute map;

map the MR calibration image in a training data pair to a predicted anatomical ROI attribute map using the deep neural network;

calculate a difference between the predicted anatomical ROI attribute map and the corresponding ground truth anatomical ROI attribute map; and adjust parameters of the deep neural network via backpropagation based on the difference between the predicted anatomical ROI attribute map and the ground truth anatomical ROI attribute map.

17. The MRI system of claim 3, wherein the processor, when executing the instructions, is configured to:

generate a graphical prescription using the localizer image; and instruct the MRI system to acquire one or more diagnostic images of the anatomical ROI of the imaging subject according to the graphical prescription.

18. The system of claim 3, further comprising determining, based on the anatomical ROI attribute map, whether the anatomical ROI matches an anatomical ROI specified by a scanning protocol, and if the anatomical ROI determined does not match the anatomical ROI specified by the scanning protocol, outputting a notification alerting an operator that the anatomical ROI does not match the anatomical ROI specified by the scanning protocol.

19. The system of claim 3, further comprising determining, based on the anatomical ROI attribute map, whether a receive radio frequency (RF) coil is positioned at a target position, and if the receive RF coil is not positioned at the target position, outputting a notification alerting an operator of the MRI system that the receive RF coil is not positioned at the target position.

20. The system of claim 3, further comprising determining, based on the anatomical ROI attribute map, whether a set field of view (FOV) of the MR calibration image matches a target FOV specified by a selected scanning protocol, and if the set FOV does not match the target FOV, outputting a notification alerting an operator that the set FOV does not match the target FOV.

\* \* \* \* \*